United States Patent
Metzen et al.

(10) Patent No.: US 12,290,768 B2
(45) Date of Patent: May 6, 2025

(54) DEVICE FOR CARRYING OUT MATERIAL EXCHANGE PROCESSES

(71) Applicant: BASF SE, Ludwigshafen am Rhein (DE)

(72) Inventors: Bernd Metzen, Ludwigshafen am Rhein (DE); Christian Kunkelmann, Ludwigshafen am Rhein (DE); Ortmund Lang, Ludwigshafen am Rhein (DE); Marvin Kramp, Ludwigshafen am Rhein (DE); Claus Hechler, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 90 days.

(21) Appl. No.: 18/012,996

(22) PCT Filed: Jun. 17, 2021

(86) PCT No.: PCT/EP2021/066379
§ 371 (c)(1),
(2) Date: Dec. 27, 2022

(87) PCT Pub. No.: WO2022/002608
PCT Pub. Date: Jan. 6, 2022

(65) Prior Publication Data
US 2023/0249098 A1  Aug. 10, 2023

(30) Foreign Application Priority Data
Jun. 29, 2020 (EP) ..................................... 20182884

(51) Int. Cl.
*B01D 3/32* (2006.01)
*B01D 3/00* (2006.01)
(Continued)

(52) U.S. Cl.
CPC ............. *B01D 3/322* (2013.01); *B01D 3/009* (2013.01); *B01D 3/36* (2013.01); *C07C 67/08* (2013.01); *C07C 67/54* (2013.01)

(58) Field of Classification Search
CPC .......... B01D 3/322; B01D 3/009; B01D 3/36; C07C 67/08
See application file for complete search history.

(56) References Cited

U.S. PATENT DOCUMENTS

| | | | | |
|---|---|---|---|---|
| 4,019,964 A | * | 4/1977 | Fickel ..................... | B01D 3/322 203/1 |
| 6,341,765 B1 | * | 1/2002 | Moser ....................... | B01D 3/32 261/109 |

(Continued)

FOREIGN PATENT DOCUMENTS

| | | |
|---|---|---|
| CN | 203861950 U | 10/2014 |
| DE | 10258329 A1 | 7/2003 |

(Continued)

OTHER PUBLICATIONS

International Preliminary Report on Patentability received for PCT Patent Application No. PCT/EP2021/066379, mailed on Jun. 20, 2022, 11 pages (5 pages of English Translation and 6 pages of Original Document).

(Continued)

*Primary Examiner* — Jonathan Miller
(74) *Attorney, Agent, or Firm* — Faegre Drinker Biddle & Reath LLP

(57) ABSTRACT

The invention relates to an apparatus for carrying out mass transfer processes, comprising a column having at least two inlet pipes for introducing a gaseous phase, where separation-active internals are accommodated in the column and a column section extends from the at least two inlet pipes to the separation-active internals, in which section a coverage of a cross-sectional area of the column is less than 25%, (Continued)

based on the total cross-sectional area, and where the at least two inlet pipes have a height offset which corresponds to not more than three times an inlet pipe diameter and the at least two inlet pipes are at an angle (α) of from 60° to 150° to one another and have asymmetry with respect to one another. The invention further relates to a use of the apparatus and also a method for designing the apparatus.

18 Claims, 8 Drawing Sheets

(51) Int. Cl.
 B01D 3/36 (2006.01)
 C07C 67/08 (2006.01)
 C07C 67/54 (2006.01)

(56) References Cited

U.S. PATENT DOCUMENTS

| | | | | |
|---|---|---|---|---|
| 6,641,700 | B1* | 11/2003 | Matsumoto | C07C 51/44 203/DIG. 21 |
| 8,888,076 | B2* | 11/2014 | Tamminen | B01D 3/008 261/109 |
| 8,926,799 | B2* | 1/2015 | Tamminen | B01D 3/06 261/78.2 |
| 8,974,640 | B2* | 3/2015 | Tamminen | B01D 3/14 261/78.2 |
| 9,895,624 | B2* | 2/2018 | Lee | B01D 3/143 |
| 2004/0182693 | A1* | 9/2004 | Matsumoto | C07C 51/44 203/99 |
| 2004/0249198 | A1 | 12/2004 | Thiel et al. | |
| 2011/0259728 | A1* | 10/2011 | Tamminen | B01D 45/08 202/158 |
| 2011/0308931 | A1* | 12/2011 | Tamminen | B01D 1/06 203/88 |
| 2011/0308932 | A1* | 12/2011 | Tamminen | B01D 1/06 261/114.5 |
| 2016/0158667 | A1* | 6/2016 | Lee | B01D 3/008 202/161 |
| 2016/0193541 | A1* | 7/2016 | Lee | B01D 3/008 202/161 |
| 2023/0249098 | A1* | 8/2023 | Metzen | C07C 67/08 203/28 |

FOREIGN PATENT DOCUMENTS

| | | |
|---|---|---|
| DE | 102005053982 A1 | 5/2006 |
| EP | 0765859 A1 | 4/1997 |
| EP | 2380645 A1 | 10/2011 |
| WO | 03/43712 A1 | 5/2003 |
| WO | 2004/063138 A1 | 7/2004 |
| WO | 2012/074818 A2 | 6/2012 |
| WO | 2017/005565 A1 | 1/2017 |
| WO | 2019/034577 A1 | 2/2019 |

OTHER PUBLICATIONS

International Search Report and Written Opinion received for PCT Patent Application No. PCT/EP2021/066379, mailed on Aug. 17, 2021, 13 pages (2 pages of English Translation and 11 pages of Original Document).

* cited by examiner

DEVICE FOR CARRYING OUT MATERIAL EXCHANGE PROCESSES

CROSS-REFERENCE TO RELATED APPLICATIONS

This application is a National stage application (under 35 U.S.C. § 371) of PCT/EP2021/066379, filed Jun. 17, 2021, which claims benefit of European Application No. 20182884.5, filed Jun. 29, 2020, both of which are incorporated herein by reference in their entirety.

The invention proceeds from an apparatus for carrying out mass transfer processes, comprising a column having at least two inlet pipes for introduction of a gaseous phase, where the at least two inlet pipes have a height offset which corresponds to not more than three times the inlet pipe diameter.

Columns for carrying out mass transfer processes having at least two inlet pipes for introduction of a gaseous phase are used particularly when large throughputs are to be realized and the column has a correspondingly large diameter. Customary column diameters are greater than 2 m. The number of inlet pipes is, in particular, dependent on the number of vaporizers required, which can have a limited construction size and different energy carriers. One inlet pipe is usually provided on the column for each vaporizer. Mass transfer processes which involve at least one gaseous phase and are carried out in columns are, for example, distillations, absorptions or gas scrubs.

U.S. Pat. No. 4,019,964 describes a method for regulating heat input to vaporizers of a distillation column and the use of two vaporizers. CN 203861950, too, mentions the use of two vaporizers.

At present, inlet pipes for introduction of a gaseous phase, which are installed essentially at the same height on the column, are usually uniformly distributed around the circumference of the column. In the case of two inlet pipes, this means that, for example, the inlet pipes are at an angle of 180° to one another.

To intensify heat and mass transfer between the different phases, it is usual to employ columns which comprise separation-active internals. In general, such processes involve at least one gaseous phase and at least one liquid phase. For the purposes of the present invention, separation-active internals are internals at which the at least one gaseous phase and the at least one liquid phase are brought into contact with one another so that an interface is enlarged and a mass transfer between the at least one gaseous phase and the at least one liquid phase is intensified. As separation-active internals, use is made of, for example, trays, which can also be referred to as mass transfer plates, structured packings or beds of packing elements. The inlet pipes for introduction of the gaseous phase are usually located below the separation-active internals. When the inlet pipes are arranged in the region of the bottom of the column, the inlet pipes are arranged below all separation-active internals comprised in the column, while in the case of them being arranged as side inlet, the inlet pipes are located between two sections, which can also be referred to as horizontal subregions of the column, having separation-active internals.

In the thermodynamic design of a column, a particular separation performance and a particular energy input are set down in order to achieve a defined separation of a mixture. This setting-down is directly coupled to a particular ratio of gaseous phase to liquid phase in the column. Local deviations in the ratio of gaseous phase to liquid phase, based on a nonuniform distribution of the gaseous phase or the liquid phase over the cross-sectional area of the column, have to be compensated for by an energy input increased to above the design figure in order to achieve the defined separation of a mixture.

Since a uniform distribution of the gaseous phase in the separation-effective internals is thus necessary in a mass transfer process in a column in order to obtain an intensive mass transfer, a uniform distribution of the vapor flow has to be realized in the region of the inlet pipes through which the gaseous phase is introduced. However, it has been found that a uniform distribution of the inlet pipes over the circumference of the column does not give an optimal distribution of the vapor flow, especially in the case of two inlet pipes, since the individual streams impinge on one another and thus lead to a loss of uniformity, i.e. form a less uniform flow.

It is therefore an object of the present invention to provide an apparatus for carrying out mass transfer processes, in which a more uniform distribution of the gaseous phase is obtained underneath the separation-active internals in the region of the inlet pipes through which the gaseous phase is introduced. A further object of the present invention is to provide for a use of the apparatus in a process, by means of which energy can be saved.

The object is firstly achieved by an apparatus for carrying out mass transfer processes, comprising a column and at least two, in particular precisely two, inlet pipes for introduction of a gaseous phase, where separation-active internals are accommodated in the column and a column section extends from the at least two inlet pipes to the separation-active internals, in which coverage of a cross-sectional area of the column is less than 25%, preferably less than 20%, more preferably less than 10% and even more preferably less than 5%, based on the total cross-sectional area of the column, and where the at least two inlet pipes have a height offset which corresponds to not more than three times an inlet pipe diameter and the at least two inlet pipes are at an angle $\alpha$ of from 60° to 150°, preferably from 80° to 130°, more preferably from 90° to 120°, for example from 95° to 115°, to one another and have asymmetry with respect to one another. The column section extends, in particular, from an uppermost edge of the at least two inlet pipes to an, in particular lowermost, entry into the separation-active internals. The column section preferably has a section height in a range from 0 to three times the inlet pipe diameter, more preferably in a range from 0.5 to 1.5 times the inlet pipe diameter. If the at least two inlet pipes have different inlet pipe diameters, these figures are based on the largest inlet pipe diameter. The section height is, in particular, the smallest distance between the separation-active internals and one of the at least two inlet pipes. The coverage of all cross-sectional areas of the column section is preferably less than 25%, more preferably less than 20%, more preferably less than 10% and even more preferably less than 5%, based on the respective total cross-sectional area of the column. In particular, the cross-sectional area of the column is free, which can also be referred to as uncovered, between the at least two inlet pipes and the separation-active internals. The column section is preferably an obstructed space and free of separation-active internals and further internals which can in each case represent coverage of the cross-sectional area, so that unhindered, spatially uniformly distributed flow, originating in the at least two inlet pipes, can be established before entry into the separation-active internals. Internals which can lead to a coverage of more than 25% and thus hindrance of the flow from the at least two inlet pipes to the separation-active internals are, for example, horizontal internals such as at least one tray such as a collection tray or a plate, for example a perforated plate, and/or vertical internals such as at least one tube, in particular with or without cap for covering, e.g. a chimney which generally prevents contact between liquid and gaseous phase, for example on a collection tray. Furthermore, the column is, in particular, a column without a dividing wall. Any fastening devices which may be present for the separation-active internals, for example support gratings which serve to fix, in particular, the packings or packing elements in the column or supports for stabilizing the trays and ducts, in particular downcomers, of separation-active trays, are considered to be part of the separation-active internals.

For the purposes of the present invention, the term asymmetry refers to inequality; for example, an asymmetric arrangement of the inlet pipes leads to different circumferential parts. The asymmetry preferably comprises or is given by the at least two inlet pipes each having a different inlet pipe diameter and/or being distributed asymmetrically around the circumference of the column. The asymmetric distribution around the circumference can also be described by the at least two inlet pipes being distributed nonuniformly around the circumference of the column.

The inlet pipe diameters of the at least two inlet pipes preferably differ by at least 10%, more preferably by at least 20% and in particular by at least 25%, based on the smallest inlet pipe diameter. The inlet pipe diameter is, in particular, the average inlet pipe diameter of the inlet pipe at the entry into the column.

The angle $\alpha$ preferably differs by at least 10°, more preferably at least 30°, even more preferably at least 60°, from a further angle $\beta$ between two of the at least two inlet pipes. In the case of precisely two inlet pipes, the angle $\alpha$ preferably differs by at least 120°, more preferably by at least 180°, from a further angle $\beta$ between the two inlet pipes. The angle $\alpha$ and the further angle $\beta$ are, in particular, angles between two adjacent inlet pipes. The angle $\alpha$ is preferably the smallest angle between two inlet pipes.

Furthermore, the asymmetry can comprise or be given by the average flow velocities through the at least two inlet pipes being different. The average velocities in the at least two inlet pipes preferably differ by at least 10%, more preferably by at least 30% and in particular by at least 45%, based on the lowest velocity. To determine the average velocity, it is possible, for example, to carry out flow measurements, in particular in the case of purely gaseous feed streams. In the case of vaporizers, the amount of steam used for heating the medium to be vaporized can, for example, also be used as proportional measure of the amount of vapor flowing through the inlet pipes.

In the case of more than two inlet pipes, the inlet pipes can preferably be at various angles to one another. Accordingly, the more than two inlet pipes are in this case distributed asymmetrically over the circumference of the column. For measurement of the height offset, the position of the midpoints of the cross sections of the respective inlet pipes is preferably used as a basis.

The at least two inlet pipes make it possible to introduce a larger amount of gaseous phase than is possible when only one inlet pipe is used. In particular, at the same amount of gaseous phase, the gaseous phase can be introduced with a lower velocity, as a result of which the energy with which the introduced streams of gaseous phase impinge on one another is reduced and a more uniform flow distribution can be achieved.

As a result of a more uniform flow distribution, energy can be saved in the mass transfer process in which the apparatus is used since local inhomogeneities in respect of the ratio of liquid phase to gaseous phase are reduced or avoided.

The axial component of the velocity of the gaseous phase on entry into the separation-active internals of the column is employed as measure of the uniform flow distribution. For this purpose, the difference between the velocity which is of such a magnitude that the velocity is greater on only 5% of the cross-sectional area and the velocity which is of such a magnitude that the velocity is lower on only 5% of the cross-sectional area is calculated. The smaller this difference, based on the average velocity, the more uniform is the flow distribution.

It has surprisingly been found that, unlike in the case of a uniform or symmetrical distribution of the at least two inlet pipes over the circumference of the column, a more uniform flow distribution can be achieved when using an arrangement of the inlet pipes having an angle in the range from 60° to 150° from one another and an asymmetry of the at least two inlet pipes. In particular, this arrangement of the at least two inlet pipes makes it unnecessary to convey and/or channel the gaseous phase entering the column below the separation-active internals through further measures such as additional internals, since a flow field which has been homogenized in respect of the flow velocity already enters the separation-active internals as a result of the targeted impingement of the flows from the at least two inlet pipes, i.e. at the corresponding angle. In the case of more than two inlet pipes, the arrangement is preferably such that the more than two inlet pipes are in each case at different angles from one another in order to obtain a more uniform flow distribution of the gaseous phase.

Mass transfer processes which can be carried out using the apparatus of the invention are all mass transfer processes in which at least one liquid phase and at least one gaseous phase participate. For the purposes of the present invention, the expression gaseous phase also encompasses a boiling phase, i.e. a phase which comprises both a liquid fraction and a gaseous fraction. Customary mass transfer processes are, for example, absorptions, distillations, rectifications, extractions or gas scrubs.

In order to keep the construction height of the column as small as possible, the at least two inlet pipes are, in a preferred embodiment, arranged at the same height on the column. Here, at the same height means that the midpoints of the at least two inlet pipes are at the same height, wherein a deviation within manufacturing tolerances is possible The arrangement of the at least two inlet pipes at the same height has the further advantage that the conditions under which the gaseous phase is introduced via the at least two inlet pipes, in particular pressure and temperature, are the same for all inlet pipes, so that no deviation in the physical properties of the gaseous phase occurs due to the height of the at least two inlet pipes.

The at least two inlet pipes through which the gaseous phase is introduced are usually arranged at the bottom of the column or as side inlet on the column. If the at least two inlet pipes are arranged as side inlet, the term "separation-active internals" in the context of the invention means the separation-active internals which are arranged next above the at least two inlet pipes. In a two-phase mass transfer process, the liquid phase usually flows from the top downward while the gaseous phase flows from the bottom upward. For this reason, liquid phase is introduced at the top of the column and the gaseous phase is introduced at the bottom and/or via side inlets. When the gaseous phase is a boiling phase, this is particularly preferably introduced via a side inlet. Phase separation then takes place in the column and the gaseous part of the boiling phase flows upward and the liquid part flows downward. Of course, it is also possible to introduce the boiling phase in the region of the bottom of the column. In this case, the gaseous part flows upward and the liquid part collects in the bottom region and is taken off from the column via a bottom offtake.

In order to intensify the mass transfer in the column, separation-active internals, preferably selected from the group consisting of trays such as dual-flow trays, cascade trays, ripple trays and crossflow trays and structured and unstructured packings and combinations thereof, are accommodated in the column. Due to the separation-active internals, continual diversion and redistribution of the liquid phase and of the gaseous phase takes place and, in addition, the phase interface is significantly increased thereby, so that a very much larger phase interface at which mass transfer occurs is obtained.

In the case of trays, a distinction is usually made between trays having guided flow of the liquid phase, e.g. crossflow trays, and trays without guided flow. In one embodiment, the separation-active internals preferably comprise trays without guided flow, e.g. dual-flow trays, ripple trays and/or cascade trays. In another embodiment, the separation-active internals comprise crossflow trays. The separation-active internals more preferably comprise exclusively trays, in particular trays without guided flow, e.g. dual-flow trays, ripple trays and/or cascade trays. Trays having guided flow have at least one downcomer for liquid, through which the liquid phase flows down onto the tray located underneath. The downcomer here acts simultaneously as feed conduit for the tray positioned under the downcomer. The downcomers of superposed trays can be arranged at positions opposite one another.

Dual-flow trays, ripple trays and cascade trays are trays without guided flow of the liquid phase. Ripple trays are also referred to as corrugated sieve trays. The liquid phase flows through openings in the tray onto the tray underneath and the gaseous phase flows from below through the openings onto the tray. It is possible here for only the gaseous phase or only the liquid phase or both the gaseous phase and the liquid phase or neither phase to flow through openings. To allow the liquid phase to flow down from the tray, the openings in a dual-flow tray do not have a chimney. Mass-transfer columns having dual-flow trays are described, for example, in WO-A 03/043712 or in WO-A 2004/063138.

Packings used can be structured packings or unstructured packings. Unstructured packings are, for example, beds of packing elements, with all customary packing elements known to a person skilled in the art being able to be used as packing elements. Suitable packing elements are, for example, rings, meshers, helichers and/or saddle bodies such as Raschig rings, IMTP® or Pall rings, Berl saddles or Intalox saddles or braids. As structured packings, it is possible to use packings having various geometric configurations, for example sheet metal packings or metal mesh packings. In one embodiment, the separation-active internals preferably comprise structured packings and/or beds of packing elements and more preferably comprise exclusively structured packings and/or beds of packing elements.

The separation-active internals are preferably made of a material comprising metal, ceramic, glass, carbon, graphite, polymer or mixtures thereof. The separation-active internals more preferably consist of metal, ceramic, glass, carbon, graphite, polymer or mixtures thereof.

The effectiveness of the separation-active internals within the apparatus for carrying out mass transfer processes should preferably correspond to at least 2 theoretical plates, for example from 2 to 40 theoretical plates. Separation performance is particularly preferably from 10 to 30 theoretical plates.

When the at least two inlet pipes are arranged as side inlet on the column, they are usually arranged between two trays or—if the separation-active internals comprise structured or unstructured packings—between two segments having separation-active internals, so that the gaseous phase is introduced below a tray or a packing and can flow uniformly from below through the tray or enter into the packing.

Both as side inlet and when the at least two inlet pipes are arranged in the region of the bottom, the at least two inlet pipes are preferably arranged at a distance below the separation-active internals which corresponds to the section height. The inlet pipe diameters of the at least two inlet pipes preferably differ by not more than a factor of 3, more preferably by a factor of 1.5, based on the smallest inlet pipe diameter. The at least two inlet pipes can have the same inlet pipe diameter. Furthermore, a ratio of the inlet pipe diameter to the column diameter is preferably not more than 0.8. If the at least two inlet pipes have different inlet pipe diameters, these figures relate to the largest inlet pipe diameter.

In a preferred embodiment, the mass transfer process carried out in the column is a distillation or rectification and the column is a distillation column or rectification column. In this case, vaporizers are preferably attached to the column via the at least two inlet pipes for introduction of the gaseous phase. More preferably, in each case one, in particular precisely one, vaporizer per inlet pipe is attached to the column. Liquid is introduced into the vaporizers, the liquid is partially or preferably completely vaporized in the vaporizer and the vapor is introduced as gaseous phase via the inlet pipes into the column. The liquid can be fed from the outside into the vaporizers or liquid phase is taken from the column and introduced into the vaporizer. A further possibility is that part of the liquid vaporized in the vaporizer is fed in from the outside and part is taken from the column. Liquid phase which is taken off from the column and fed to the vaporizers can, for example, be taken off at the bottom of the column. When the vaporizer is used as intermediate vaporizer, preference is given to the liquid phase being taken off from the column via a side offtake, for example from one tray, and fed to the vaporizer.

A further possibility is that one vaporizer is used for vaporizing liquid introduced from the outside and a second vaporizer is used for vaporizing liquid phase which is taken off from the column. However, preference is in this case given to feeding the liquid introduced from the outside and the liquid phase taken off from the column to each vaporizer, with the liquids either being mixed before introduction into the vaporizer or being introduced into the vaporizer via separate conduits and mixed in the vaporizer.

As vaporizers, it is possible to use any type of vaporizer known to a person skilled in the art which is suitable for the mass transfer process, in particular the distillation or rectification. Suitable vaporizers are, for example, shell-and-tube vaporizers and plate vaporizers. The vaporizers can be configured as falling film evaporator, forced convection vaporizer, forced convection expansion vaporizer, helical tube vaporizer, kettle-type vaporizer or natural convection vaporizer.

In a preferred embodiment of the invention, the at least two inlet pipes open radially into the column. This is in particular to be understood to the effect that extensions of the central axes of the at least two inlet pipes intersect the central axis of the column. The inlet pipes can terminate with the column wall or extend into the column; the inlet pipes preferably terminate with the column wall. As a result of an arrangement of the at least two inlet pipes in such a way that they are at different angles α or β to one another, and/or have different inlet pipe diameters or flow velocities, the vapor streams fed in do not impinge symmetrically on one another. This gives rise to a more uniform vapor flow in the column and there is no concentration of vapor in the middle of the column.

As an alternative to the radial arrangement, it is also possible for the at least two inlet pipes to open into the column at an opening angle to the radial direction.

The at least two inlet pipes through which the gaseous phase is introduced can have any cross-sectional shape. However, preference is given to the at least two inlet pipes having a circular or elliptical cross section. The cross-sectional area of the at least two inlet pipes is dependent on the amount of gaseous phase to be introduced. It is possible for the cross-sectional area of the at least two inlet pipes arranged at essentially the same height to be essentially the same. Here, "essentially the same" means that the cross-sectional areas can differ in magnitude as a result of manufacturing tolerances. The shape of the cross-sectional areas of the at least two inlet pipes arranged essentially at the same height is also preferably the same.

As an alternative, it is of course also possible for cross-sectional area and/or cross-sectional shape of the at least two inlet pipes arranged at essentially the same height to be different. Different cross-sectional shapes enable local structural conditions to be taken into account. Different cross-sectional areas serve to match the vaporizers to different energy sources which have a different energy content, for example in the case of heat integration. In heat integration, part of the required heat from a further heat source is taken directly from the process. Since the available quantity of heat from the integration and the remaining required quantity of heat can be very different, the respective inlet pipes have different cross-sectional areas here. Furthermore, the cross-sectional area can be selected as a function of the size of the vapor stream to be fed in.

In order to find the best orientation of the at least two inlet pipes relative to one another, it is advantageous for the arrangement of the at least two inlet pipes to be calculated by means of a mathematical simulation. A method suitable for this purpose comprises the following steps:
(a) specification of the position and orientation of the at least two inlet pipes on the column;
(b) calculation of the gas flow in the column using a flow simulation;
(c) repetition of the steps (a) and (b) with different positions and orientations of the at least two inlet pipes and
(d) selection of the position and orientation of the at least two inlet pipes at the flow which displays the most uniform flow pattern.

For the flow simulation, it is possible to use all simulation programs known to those skilled in the art. Numerical simulations based on finite elements or finite volumes, preferably based on finite volumes, are particularly suitable here. A suitable simulation program is, for example, the commercially available ANSYS Fluent®, which operates on the basis of finite volumes. The flow in the column can be depicted graphically with the aid of the flow simulation and the positions of the at least two inlet pipes relative to one another can be optimized on the basis of the result. In the case of different cross-sectional shape and/or cross-sectional area of the at least two inlet pipes, the optimum size and shape of the cross-sectional area of the at least two inlet pipes, which lead to the most uniform flow distribution in the column, can also be determined by means of the flow simulation.

Furthermore, the use of the apparatus for carrying out mass transfer processes for the production, in particular for the continuous production, of isocyanates, styrene or an alkyl acrylate, in particular a butyl acrylate, or in crackers, in particular for the dissociation of $C_3$-hydrocarbons, is proposed. The use of the apparatus for carrying out mass transfer processes for the continuous production of the alkyl acrylate is particularly advantageous since the process is distinguished by a high energy consumption.

The apparatus for carrying out mass transfer processes is advantageously used in a process for the continuous production of a butyl acrylate $H_2C=CH-C(=O)OR$, where R=n-butyl or isobutyl.

Alkyl acrylates can be produced from 3-hydroxypropionic acid, as described, for example, in WO 2019/034577. As an alternative, acrylic acid can be used for producing the butyl acrylate.

3-hydroxypropionic acid can firstly be esterified with an alcohol in a first step and the resulting 3-hydroxypropionic ester can then be dehydrated in a subsequent step to give the corresponding alkyl acrylate. As an alternative, 3-hydroxypropionic acid can also firstly be dehydrated in a first step and the resulting acrylic acid can then be esterified with an alcohol in a subsequent step.

Preference is given to reacting aqueous 3-hydroxypropionic acid in the presence of the alcohol n-butanol in the process for the continuous production of the butyl acrylate ($H_2C=CH-C(=O)OR$, where R=n-butyl or isobutyl).

The apparatus according to the invention for carrying out mass transfer processes is also preferably used as rectification column in the process for the continuous production of alkyl acrylate ($H_2C=CH-C(=O)OR$, where R=n-butyl or isobutyl), with aqueous 3-hydroxypropionic acid being reacted under dehydrating and esterifying conditions in the presence of the appropriate butanol (R—OH) in a reactor comprising the rectification column and butyl acrylate formed, unreacted butanol and water which has been used and has been formed being distilled off at the top as ternary azeotrope and, after separation into a respectively liquid aqueous phase and liquid organic phase, the aqueous phase and the organic phase each being at least partly discharged and the organic phase comprising the butyl acrylate and the butanol being fractionally distilled.

A virtually acetate-free butyl acrylate can be produced by use of 3-hydroxypropionic acid. Here, "acetate" is n-butyl or isobutyl acetate [$H_3C-C(=O)-OR$].

The 3-hydroxypropionic acid used is preferably bio-based 3-hydroxypropionic acid. For the purposes of the present invention, a "bio-based 3-hydroxypropionic acid" is a 3-hydroxypropionic acid which has been produced from renewable raw materials. Furthermore, the bio-based 3-hydroxypropionic acid has preferably been produced by fermentation, in particular from glucose, xylose, arabinose, sucrose, fructose, cellulose, glucose oligomers and/or glycerol by fermentation, in particular with subsequent purification. For example, the production of bio-based 3-hydroxypropionic acid, also referred to as bio-3-hydroxypropionic acid or bio-HPS, from sugars such as glucose by fermentation and subsequent purification is known from WO 2012/074818 A2.

The aqueous bio-3-hydroxypropionic acid produced in this way comprises, for example, water and essentially the following constituents:

from 35 to 70% by weight of 3-hydroxypropionic acid,
from 0 to 20% by weight of oligomeric 3-hydroxypropionic acid,
from 0 to 10% by weight of acrylic acid,
from 0 to 1% by weight of oligomeric acrylic acid,
from 0.01 to 0.1% by weight of glycolic acid,
from 0.01 to 0.1% by weight of 2-hydroxypropionic acid,
from 0.005 to 0.05% by weight of formic acid,
from 0 to 0.15% by weight, in particular from 0.0 to 0.05% by weight, e.g. from 0.005 to 0.10% by weight, of acetic acid,
from 0.005 to 0.05% by weight of succinic acid,
from 0.005 to 0.05% by weight of fumaric acid,
from 0.0001 to 0.01% by weight of formaldehyde,
from 0.0001 to 0.01% by weight of acetaldehyde,
from 0.0001 to 0.01% by weight of methanol and
from 0.0001 to 0.01% by weight of ethanol.

The molar ratio of butanol used to 3-hydroxypropionic acid used is preferably at least 1 and is also preferably below 5. A molar ratio of butanol used to 3-hydroxypropionic acid used is particularly advantageously in the range from 1:1 to 3:1. Very particular preference is given to a molar use ratio in the range from 1.1:1 to 1.8:1.

The dehydrating and at the same time esterifying conditions are preferably provided by the presence of a catalytically active amount of an acid. The content of catalytically active acid in the reactor, based on the reaction mixture present therein, is advantageously from 0.1% by weight to 20% by weight, more preferably from 5% by weight to 15% by weight, in particular from 7% by weight to 10% by weight. Preferred acids are inorganic acids such as sulfuric acid and phosphoric acid, and also organic sulfonic acid. Among organic sulfonic acids, preference is given to methanesulfonic acid, benzenesulfonic acid, dodecylbenzenesulfonic acid and/or p-toluenesulfonic acid. It is also possible to use a mixture of in each case at least one organic sulfonic acid and inorganic acid, for example sulfuric acid. Particular preference is given to using sulfuric acid and/or organic sulfonic acid(s) as esterification and dehydration catalyst(s).

The reaction of the reactants, i.e. the starting materials 3-hydroxypropionic acid and butanol, in the reactor is preferably carried out at a temperature in the range from 80° C. to 170° C., more preferably in the range from 100° C. to 155° C., even more preferably in the range from 120° C. to 140° C. The residence time of the reactants, i.e. the starting materials 3-hydroxypropionic acid and butanol, in the reactor is preferably from 1 hour to 20 hours, more preferably from 2 hours to 8 hours. For the purposes of the present invention, the residence time is the time for which a quantity to be taken off at the bottom of the reactor resides in the liquid volume of the reactor.

In the simplest case, the rectification column is placed directly on top of the reactor, with the vapor ascending from the reactor, i.e. the gaseous phase, generally being conveyed in countercurrent to the runback, i.e. the liquid phase, fed into the rectification column. The directly superposed rectification column offers the advantage of conveying the vapor rising in the reactor directly without additional piping into the rectification column and conveying the liquid phase running down in the rectification column directly into the reactor.

As an alternative, it is possible to have a separate arrangement of reactor and rectification column, with appropriate piping for feeding the gaseous phase into the rectification column and for discharging the liquid phase flowing through the rectification column into the reactor. Such an embodiment with indirectly superposed column is also encompassed by the term "reactor with rectification column".

The pressure at the top of the rectification column is preferably in the range from 0.2 bar to 5.0 bar, more preferably in the range from 0.3 bar to 3.0 bar, in particular in the range from 0.5 bar to 1.2 bar.

The separation into an aqueous phase and an organic phase is preferably carried out by means of a phase separator. In such an apparatus, two liquids which are not homogeneously miscible with one another can be separated by means of their density difference. Preference is given to discharging at least part of the aqueous phase obtained, which comprises water together with butanol and possibly traces of further components. Particular preference is given to discharging from 10% by weight to 80% by weight, more particularly from 20% by weight to 70% by weight, of the aqueous phase obtained. The remainder is in each case preferably recirculated to the rectification column. Part of the organic phase obtained is preferably likewise recirculated, preferably to the rectification column. Preference is given to recirculating from 0% by weight to 80% by weight, for example from 1% by weight to 75% by weight, more preferably from 5% by weight to 50% by weight, of the organic phase, preferably to the rectification column. The other part is preferably discharged and passed to fractional distillation.

The fractional distillation of the discharged organic phase comprising the butyl acrylate and the butanol is preferably carried out in such a way that the butanol is separated off overhead in a downstream rectification column, as described, for example, in EP 765 859 A1. The apparatus of the invention for carrying out mass transfer processes can be used for the fractional distillation of the discharged organic phase. The column which is comprised by the apparatus of the invention for carrying out mass transfer processes can be used as the downstream rectification column. The butanol which has been separated off in this way is preferably recirculated to the reactor. The recirculation is advantageously carried out continuously, with or without intermediate vessels.

The fractional distillation of the organic phase comprising the butyl acrylate and the butanol is preferably carried out in such a way that the butanol is distilled off in an additional rectification column and the butyl acrylate is distilled off from the resulting bottoms in a further additional rectification column.

The resulting bottoms from the additional rectification column consist essentially of the butyl acrylate and small amounts of high boilers and a stabilizer which is used and can also be referred to as process stabilizer and, for example, comprises or consists of phenothiazine (PTZ).

In a further downstream rectification column, the butyl acrylate is usually separated off at the top. The apparatus of the invention for carrying out mass transfer processes can be used for separating off the butyl acrylate. The column which is encompassed by the apparatus of the invention for carrying out mass transfer processes can be used as the further downstream rectification column. During condensation, a stabilizer, in particular a storage stabilizer such as p-methoxyphenol (MeHQ), is preferably added. The bottoms comprising relatively high-boiling by-products from this further downstream rectification column is advantageously preferably recirculated to the reactor, preferably continuously with or without intermediate vessels.

A particular embodiment comprises taking off the butyl acrylate from the downstream rectification column for recovering butanol via a side offtake after removal of any entrained liquid droplets and condensing it to give the pure ester. A stabilizer, in particular a storage stabilizer such as MeHQ, is added to the ester in the condensation. In this variant, the bottoms from the downstream rectification column, which consist essentially of butyl acrylate, are preferably conveyed back into the reactor. The butanol obtained after the separation is particularly advantageously at least partly recirculated to the reaction in the reactor. Preference is given to recirculating from 5% by weight to 100% by weight, more preferably from 80% by weight to 100% by weight, of the butanol.

n-butyl acrylate can be produced in a purity of, in particular, ≥99.0% by weight, more preferably ≥99.5% by weight, and with a content of n-butyl acetate of ≤1000 ppm, more particularly ≤100 ppm, by means of the process for the continuous production of the butyl acrylate $H_2C=CH-C(=O)OR$, where R=n-butyl. In particular, the content of acrylic acid is <100 ppm, e.g. from 5 to 80 ppm.

Isobutyl acrylate can be produced in a purity of, in particular, ≥99.0% by weight, more particularly ≥99.5% by weight, and with a content of isobutyl acetate of ≤1000 ppm, more particularly ≤100 ppm, by means of the process for the continuous production of the butyl acrylate $H_2C=CH-C(=O)OR$, where R=isobutyl. In particular, the content of acrylic acid is <100 ppm, e.g. from 5 to 80 ppm.

In the process for the continuous production of the butyl acrylate $H_2C=CH-C(=O)OR$, where R=n-butyl or isobutyl, the butyl acrylate formed is preferably stabilized by suitable polymerization inhibitors in order to avoid undesirable polymerization. The process is preferably carried out in the presence of effective amounts of a stabilizer or a plurality of stabilizers. Suitable stabilizers are in principle all polymerization inhibitors which are recommended for stabilizing acrylic acid and acrylic esters in, for example, DE 10 2005 053 982 A1 and DE 102 58 329 A1. Suitable stabilizers can be, for example, N-oxides (nitroxyl or N-oxyl free radicals, i.e. compounds which have at least one N—O group), e.g. 4-hydroxy-2,2,6,6-tetramethylpiperidine-N-oxyl (4HT) or 4-oxo-2,2,6,6-tetramethylpiperidine-N-oxyl, phenols and naphthols such as p-methoxyphenol, p-aminophenol, p-nitrosophenol, 2-tert-butylphenol, 4-tert-butylphenol, 2,4-di-tert-butylphenol, 2-methyl-4-tert-butylphenol, 2,6-tert-butyl-4-methylphenol or 4-tert-butyl-2,6-dimethylphenol, quinones such as hydroquinone or hydroquinone monomethyl ether, aromatic amines such as N,N-diphenylamine, phenylenediamines such as N,N'-dialkyl-p-phenylenediamine, where the alkyl radicals can be identical or different and each have, independent of one another, from 1 to 4 carbon atoms and can be linear or branched, e.g. N,N'-dimethyl-p-phenylenediamine or N,N'-diethyl-p-phenylenediamine, hydroxylamines such as N,N-diethylhydroxylamine, imines such as methylethylimine or methylene violet, sulfonamides such as N-methyl-4-toluenesulfonamide or N-tert-butyl-4-toluenesulfonamide, oximes such as aldoximes, ketoximes or amidoximes, e.g. diethyl ketoxime, methyl ethyl ketoxime or salicylaldoxime, phosphorus-comprising compounds such as triphenylphosphine, triphenyl phosphite or triethyl phosphite, sulfur-comprising compounds such as diphenyl sulfide or phenothiazine, metal salts such as cerium(III) acetate or cerium(II) ethylhexanoate, but also various copper salts such as Cu(II) dialkyldithiocarbamates, e.g. Cu(II) dibutyldithiocarbamate, and also Cu(II) oxinate (oxine=4-hydroxyquinoline), in addition manganese salts such as Mn(II) diacetate, or mixtures thereof. Stabilization is preferably effected using phenothiazine (PTZ), MeHQ, hydroquinone, hydroquinone monomethyl ether, 4-hydroxy-2,2,6,6-tetramethylpiperidine-N-oxyl, 4-oxo-2,2,6,6-tetramethylpiperidine-N-oxyl, 2,6-tert-butyl-4-methylphenol or mixtures thereof. Very particular preference is given to using phenothiazine (PTZ) and/or MeHQ and/or 4-hydroxy-2,2,6,6-tetramethylpiperidine-N-oxyl (4HT) as polymerization inhibitor.

Even though the inhibitors can be added as pure substance, it is advantageous to add the inhibitor dissolved in a solvent as solution which can be metered simply and reproducibly, where the inhibitor mixtures in a single solution are also possible in principle. A liquid which is in any case present in the acrylate synthesis process or in the mixture in the rectification column is preferably used as solvent. Particularly preferred choices for the solvent are the acrylate product (i.e. the butyl acrylate) itself, water or one of the synthesis starting materials for the acrylate (e.g. the butanol).

Particularly at the lower end of the rectification column, the liquid flowing down in the rectification column, i.e. the liquid phase, is preferably at least partly taken off from the rectification column, at least partially vaporized in at least one vaporizer, preferably in at least two, for example precisely two, vaporizers and at least partly recirculated via the at least two inlet pipes into the rectification column.

The process for the continuous production of the butyl acrylate $H_2C=CH-C(=O)OR$, where R=n-butyl or isobutyl, is advantageously carried out using particular measures for controlling particular parameters. This process control is preferably carried out as follows: For the production of in-specification butyl acrylate, i.e. a product having a high purity of, in particular, more than 99% by weight, the separation of acrylic acid from the butyl acrylate in the rectification column is of critical importance. Here, it has been found to be advantageous to set a defined ratio between the organic runback and the aqueous runback. This reflux ratio of the streams is preferably in the range from 0.1 to 1.0.

Furthermore, the reaction volume in the bottom of the rectification column or the stand-alone reactor with indirectly superposed rectification column, which is decisive for the conversion, is preferably kept constant or virtually constant. For the purposes of the present invention, virtually constant means that there is a deviation of up to +/−10% by volume inclusive. This can be achieved firstly by a constant or virtually constant liquid stream being discharged from the reaction volume at a constant or virtually constant liquid level in the reactor. In addition, the amount taken off at the bottom preferably has a particular ratio to the inflow, preferably a ratio of the amount taken off at the bottom to inflow in the range from 0.01 to 0.30.

A second measure is quality control in respect of the acrylic acid content in the organic distillate. Since the liquid volume in the reaction space reacts sharply to the amount of aqueous runback, the liquid level in the reactor is preferably regulated by means of the runback amount, which corresponds to the recirculation amount, of the aqueous phase.

The aqueous runback ensures that the high boilers n-butyl acrylate and isobutyl acrylate and the corresponding butanol can be distilled off due to the formation of a low-boiling azeotrope. The organic runback ensures that the concentration of the acrylic acid formed in the reactor remains below the concentration of, in particular, 100 ppm.

The control of the amount of the organic runback enables a number of effects such as purification by distillation, increase in the residence time in the reaction space, increase in the concentration of butanol in the reaction space to be combined. This regulation strategy leads to particularly stable operation in the reactor and in the rectification column.

As a result of the improved regulation concept, an even higher yield of butyl acrylate can be produced at a lower energy consumption and with a further-improved quality, in particular improved purity.

In a preferred embodiment, at least one first stabilizer which dissolves in active proportions both in the aqueous phase and in the organic phase is present in the rectification column. Such a stabilizer, such as in particular 4HT, is particularly introduced above the uppermost theoretical plate of the rectification column. In this way, the entire rectification column is stabilized by means of the stabilizer.

Furthermore, at least one further stabilizer which dissolves in effective proportions both in the aqueous phase and in the organic phase is preferably introduced into the phase separator which collects the condensate and/or into the conduit of a quenching circuit and/or at the top of the condenser. This further stabilizer is preferably the same as the first stabilizer and is, in particular, 4HT.

The quenching circuit (i.e. the liquid return stream of part of the condensate, e.g. from 10 to 50 hundredths by weight of the condensate, into the condenser) which is preferably provided has the function of particularly adequately stabilizing the naturally stabilizer-free vapor during condensation in the condenser.

Effective stabilizer amounts present in solution in the respective phase are in total particularly ≥10 ppm by weight, e.g. in the range from 10 to 1000 ppm by weight.

If a stabilizer used does not dissolve completely in the respective liquid phase, it is correspondingly present in suspension. If a stabilizer is present as suspension in the liquid phase or phases, this particulate stabilizer fraction which is a priori barely or not active can offer advantages due to its action as stabilizer depot since, for example, in the case of chemical degradation of dissolved stabilizer, which impairs the effectiveness thereof, further freshly active stabilizer additionally goes into solution from the suspended fraction, which can occur even between phases in the presence of appropriately intimate contact of the liquid phases and can be influenced via the size distribution of the particles.

The stabilizers can in each case be used as, in particular, a solution in a suitable solvent, in particular as indicated above, e.g. the alcohol used in the process, i.e. butanol, water, the corresponding butyl acrylate, e.g. in each case as 1-5% strength by weight solution.

A second stabilizer, in particular PTZ, which is suitable for relatively high temperatures and a third stabilizer, in particular MeHQ, which owing to its relatively high vapor pressure also stabilizes the transition region between reaction space and lower part of the column is advantageously introduced into the reactor. The second and third stabilizers can in each case be used, in particular, as solution in a suitable solvent, in particular as indicated above, e.g. the butyl acrylate appropriately formed in the process or in the starting materials 3-hydroxypropionic acid or butanol which are used.

An oxygen-comprising gas is advantageously additionally used to inhibit polymerization. Air/nitrogen mixtures, e.g. having an oxygen content of from 4% by volume to 9% by volume, are particularly suitable for this purpose. If an oxygen-comprising gas is used for inhibiting polymerization, it is preferably introduced at the lower end of the vaporizer or at the lower end of the reactor.

The start-up of the process for the continuous production of the butyl acrylate ($H_2C=CH-C(=O)OR$, where R=n-butyl or isobutyl) comprising the reaction in the reactor and the distillation in the rectification column can suffer from problems since, in particular, changes in the runback amounts of the various streams have greatly different effects on the total system. Changes in the amount of the aqueous runback have a relatively quick effect the amount of vapor formed and changes in the amount of the organic runback have a relatively slow effect on the acrylic acid concentration in the top of the column. However, the two runback amounts are not independent of one another. When the precise runback amounts are not matched well to one another, vaporization can cease or the rectification column becomes flooded due to an excessively large amount of vapor. It is then very difficult to bring the system back into the normal operating state.

For this reason, the reactor is advantageously firstly filled with an appropriate amount of a suitable reaction mixture comprising the butyl acrylate, in particular bottom product from a previous production campaign, or the appropriate butyl acrylate for start-up. The bottom is then heated to operating temperature, i.e. reaction temperature, and the feed streams of 3-hydroxypropionic acid, butanol and catalyst are brought into operation.

Further-increased yields and/or product purities can be achieved by means of the particular start-up strategy and/or the particular stabilizing concept.

All pressures indicated are absolute pressures. All ppm figures are by weight.

Working examples of the invention are illustrated in the figures and are explained further in the following description.

BRIEF DESCRIPTION OF FIGURES

FIGS. 1 to 5 show cross-sectional views of a column 2 having various arrangements of inlet pipes 3, 5.

In FIG. 1, in accordance with the prior art, a first inlet pipe 3 and a second inlet pipe 5 are arranged at an angle α of 180° on the column 2. Furthermore, the inlet pipes 3, 5 are oriented in a radial direction 4 on the column 2.

The columns 2 depicted in FIGS. 2 and 3 also have precisely two inlet pipes 3, 5. Here, the angle α between the two inlet pipes 3, 5 is less than 180°. In FIG. 2, the angle α is 90° and in FIG. 3 the angle α is 120°. A further angle β between the two inlet pipes 3, 5 is 270° in FIG. 2 and 240° in FIG. 3. Accordingly, the two inlet pipes 3, 5 have inequality with one another owing to their nonuniform distribution around the circumference 19 of the column 2, since circumference sections having different lengths are formed between the inlet pipes 3, 5.

Figure 1:
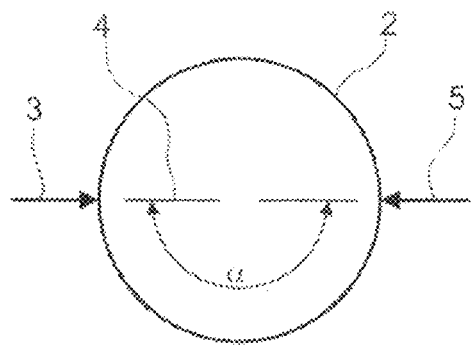
FIGS. 1 to 5 cross-sectional views of a column having various inlet pipe arrangements, FIG. 6 a three-dimensional depiction of a column having two inlet pipes, FIG. 7 a three-dimensional depiction of a column having two inlet pipes of different diameter, FIG. 8 a longitudinal sectional view of the column with inlet pipe, FIG. 9 a histogram depicting the relative velocity on entry into separation-active internals in the form of a packing, FIG. 10 frequency functions of the relative velocity on entry into separation-active internals in the form of a packing for different inlet pipe arrangements, FIG. 11 frequency functions of the relative velocity on entry into separation-active internals in the form of trays for different inlet pipe arrangements, FIG. 12 frequency functions of the relative velocity on entry into separation-active internals in the form of trays for different inlet pipe arrangements and unequal flow velocities in the inlet pipes, FIG. 13 frequency functions of the relative velocity on entry into separation-active internals in the form of trays for different inlet pipe arrangements and unequal inlet pipe diameters, FIG. 14 frequency functions of the relative velocities for one and two inlet pipes and FIG. 15 a schematic depiction of an apparatus for carrying out mass transfer processes.
Figure 2:
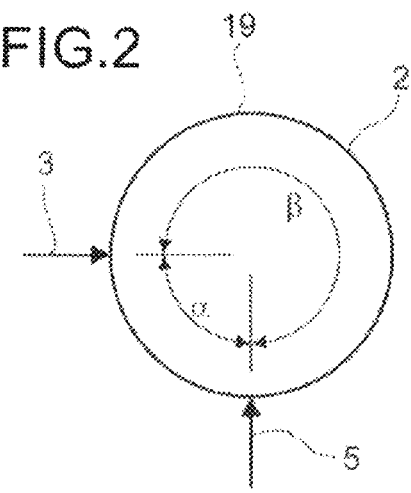
Figure 3:
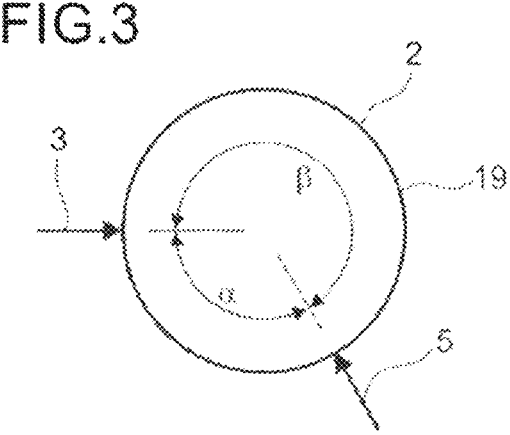
Figure 4:
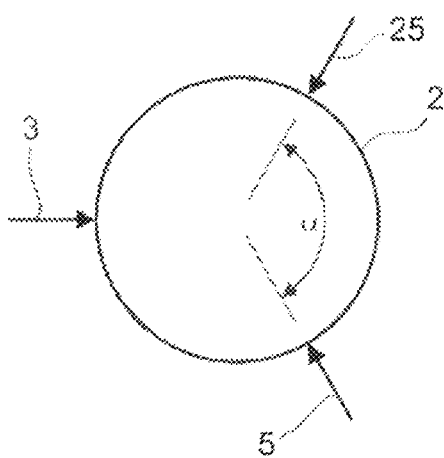

Three inlet pipes 3, 5, 25 for introduction of a gaseous phase are arranged on the column 2 in FIG. 4. The angle α between the inlet pipes 3, 5, 25 is 120° in each case and the inlet pipes 3, 5 are uniformly distributed over the circumference 19. This is an embodiment according to the prior art in so far as equal inlet pipe diameters 6, 17 and equal velocities in the inlet pipes 3, 5, 25 are present. In the case of at least two different inlet pipe diameters 6, 17 and/or at least two different velocities through the inlet pipes 3, 5, 25 arranged as depicted, an embodiment according to the invention is present.

Figure 5:
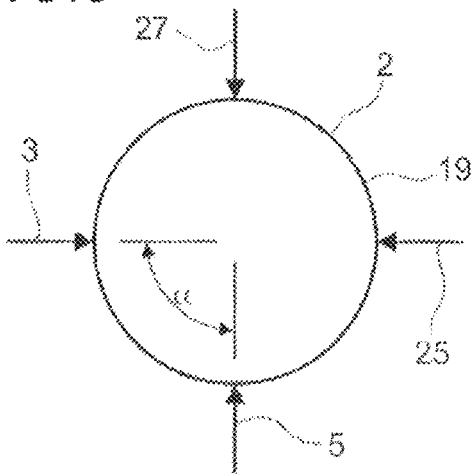

FIG. 5 shows a column 2 having four inlet pipes 3, 5, 25, 27. These are uniformly distributed around the circumference 19 of the column 2 and the angle α between the inlet pipes 3, 5, 25, 27 is 90° in each case. This is likewise an embodiment according to the prior art, in so far as equal inlet pipe diameters 6, 17 and equal velocities in the inlet pipes 3, 5, 25, 27 are present. In the case of at least two different inlet pipe diameters 6, 17 and/or at least two different velocities through the inlet pipes 3, 5, 25, 27 arranged as depicted, an embodiment of the invention is present.

Figure 6:
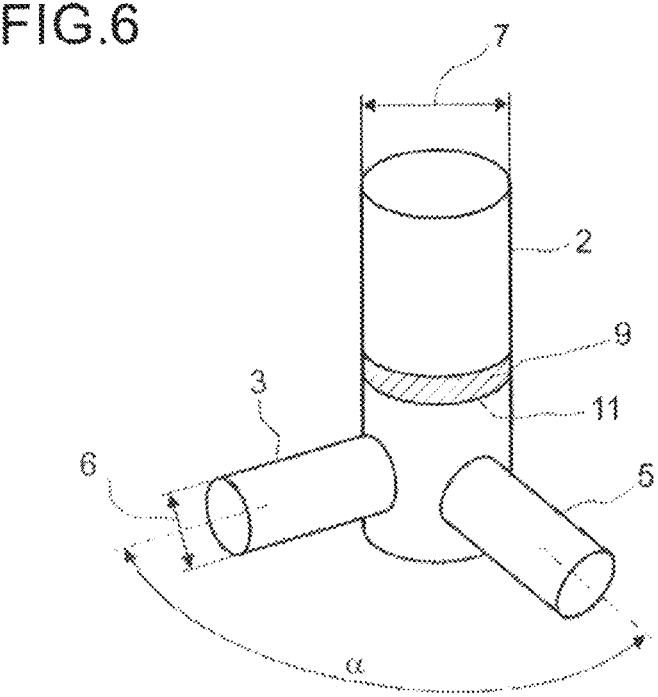

FIG. 6 shows a three-dimensional depiction of a column 2 having two inlet pipes 3, 5. To give a better overview, only the region of the column 2 in which the inlet pipes 3, 5 are arranged is shown.

Two inlet pipes 3, 5 for introduction of a gaseous phase are arranged on the column 2. The inlet pipes 3, 5 are at an angle α in the range from 60° to 150° to one another. In the embodiment depicted here, the angle α is 90°. In particular, no inlet pies 3, 5 are arranged directly opposite one another in the arrangement of the inlet pipes 3, 5. Furthermore, it is advantageous when more than two inlet pipes 3, 5 are provided that the angles between the inlet pipes 3, 5 are different. As a result of this, direct impingement of the gaseous phases introduced via the inlet pipes 3, 5 is avoided and a more uniform flow distribution is achieved in this way.

Above the inlet pipes 3, 5 for introducing the gaseous phase, there are separation-active internals 9 in the form of a packing having an entry 11 in the column 2.

Figure 7:
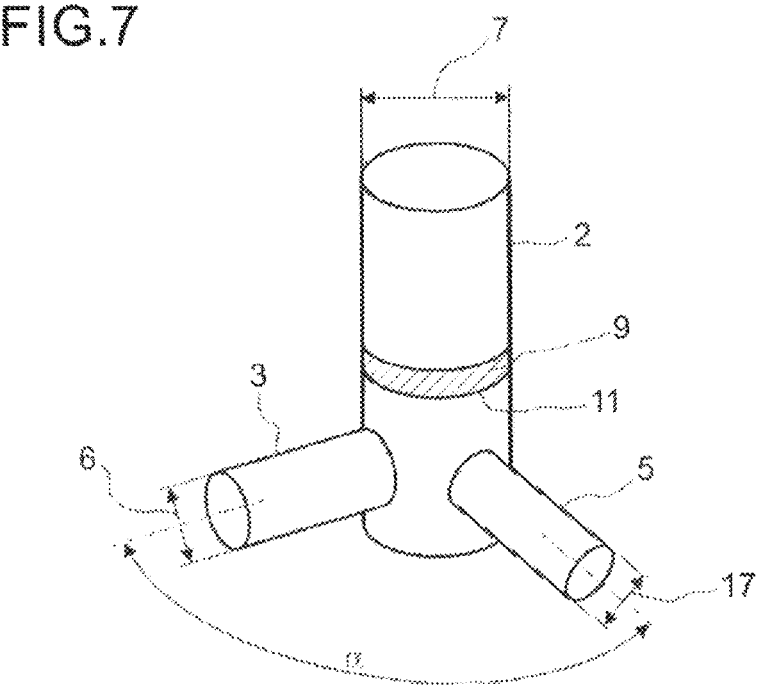

FIG. 7 shows a three-dimensional depiction of a column 2 having two inlet pipes 3, 5, which essentially corresponds to the column 2 according to FIG. 6, the difference being that in this case inlet pipes 3, 5 have different inlet pipe diameters 6, 17. The first inlet pipe 3 has an inlet pipe diameter 6 larger than a further inlet pipe diameter 17 of the second inlet pipe 5.

Figure 8:
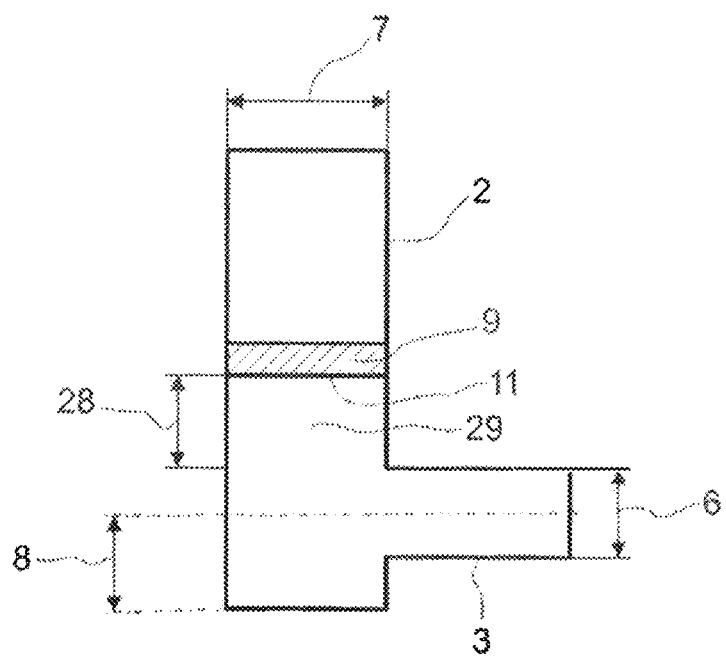

FIG. 8 shows a longitudinal sectional view of the column 2 according to FIG. 6, which has a column section 29 and inlet pipes 3, 5. The column section 29 has a free cross-sectional area and has a section height 28. The inlet pipes 3, 5 have the inlet pipe diameter 6 and are each arranged at a height 8 on the column 2 which has a column diameter 7.

EXAMPLES AND COMPARATIVE EXAMPLES

Example 1

The distribution of the relative velocity at the entry 11 into a packing 9 of a column 2 was determined. The calculation is based on an arrangement of two inlet pipes 3, 5 arranged at the same height at an angle α of 120° from one another.

For the calculation of the vapor flow presented here, a packing having a height of 1 m and a pressure drop of 1 mbar was assumed as separation-active internals 9. The column diameter 7 of the column 2 of 3200 mm and the inlet pipe diameter 6 of the two inlet pipes 3, 5 of 1000 mm was assumed for the calculation. A pressure in the column 2 of 5.5 bar, a gas density of 16.6 kg/m$^3$, a gas viscosity of 1.3·10$^{-5}$ Pa·s, a velocity in the inlet pipes 3, 5 of 1.07 m/s with an F factor of 4.34 and a velocity in the column 2 of 0.21 m/s with an F factor of 0.85 were prescribed as boundary conditions for the calculation of the velocities. The F factor refers to the steam loading in the column 2 and is the product of the average velocity of the gaseous phase in m/s multiplied by the square root of the gas density in kg/m$^3$.

In the interior of the column 2, a system of a plurality of eddy structures which are not shown here and in which flow lines, likewise not shown here, move upward in the direction to the separation-active internals 9, i.e. the packing, is established.

The vertical velocity component at the entry 11 of the separation-active internals 9 is a measure of the incorrect distribution established in the column 2.

In order to be able to employ the incorrect distribution appropriately as a measure of the flow uniformity, it is useful firstly to depict the calculated vertical velocities at the entry 11 of the column 2 in a histogram. Such a histogram is shown by way of example in FIG. 9.

To produce the histogram, it is possible, for example, firstly to depict the vertical velocities at the entry 11 into the separation-active internals 9 calculated using a suitable simulation program for flow calculations graphically by means of a grayscale and generate the histogram from the shades of gray. The histogram shows, for each velocity, the proportion of the cross-sectional area in which this velocity occurs. Here, the velocity is plotted on the abscissa 21 and the cross-sectional area is plotted on the ordinate 23.

Example 2

Figure 9:
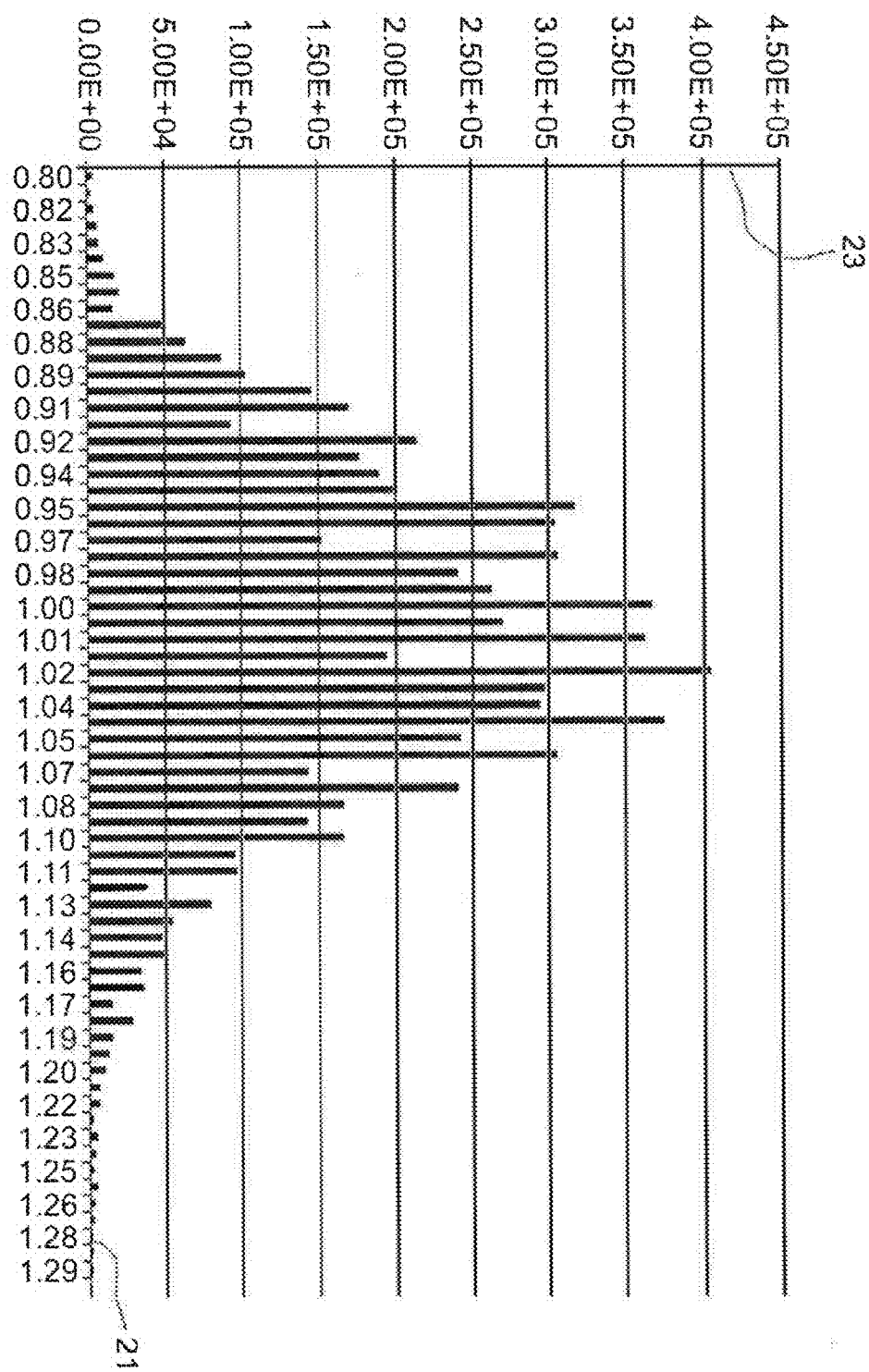

A cumulated frequency function as shown in each case in FIGS. 10 to 14 for different inlet pipe arrangements, inlet pipe configurations and modes of operation was calculated from histogram data as depicted in FIG. 9. The difference between the velocity which is of such a magnitude that the velocity is greater on only 5% of the cross-sectional area and the velocity which is of such a magnitude that the velocity is lower on only 5% of the cross-sectional area is calculated as measure for the nonuniform distribution. The smaller this difference, the more uniform is the flow distribution.

Figure 10:
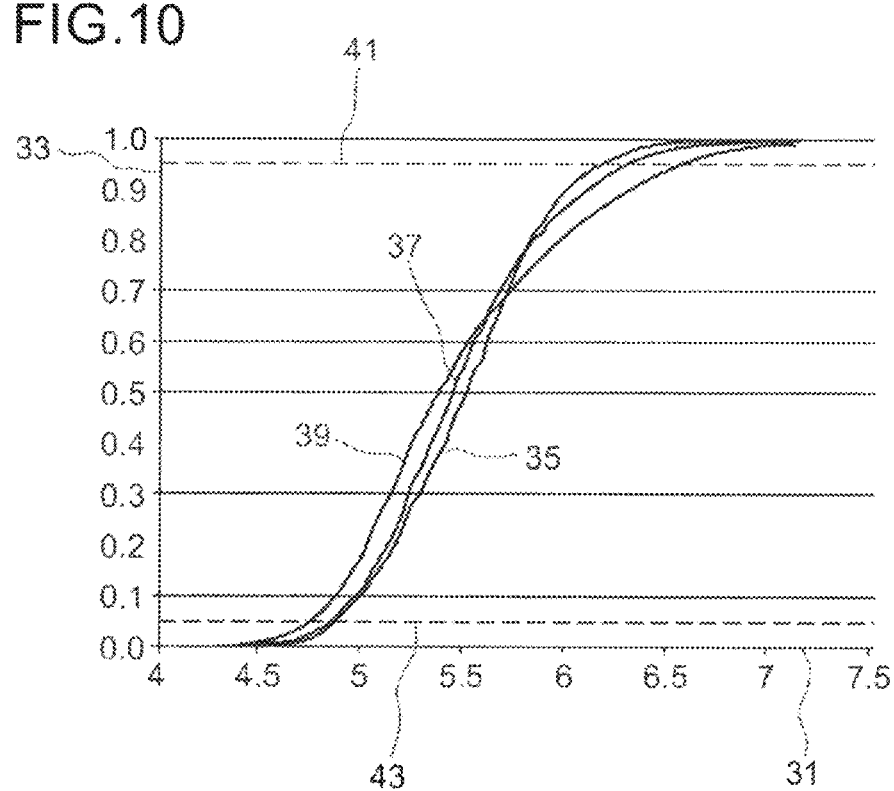

FIG. 10 shows frequency functions of the relative velocity at the entry 11 into the separation-active internals 9, i.e. the packing, for different arrangements of the inlet pipes 3, 5. Here, the velocity is plotted on the abscissa 31 and the cumulated proportion by area from 0 (no proportion at all) to 1 (the total area) is plotted on the ordinate 33.

In a first arrangement, the angle α between the inlet pipes 3, 5 is 90°. The corresponding first curve of the frequency function is designated by the reference symbol 35. A second curve 37 shows the frequency function for an arrangement of the inlet pipes 3, 5 at an angle α of 120° and a third curve 39 shows the frequency function for an arrangement of the inlet pipes 3, 5 at an angle α of 180°.

In contrast to the histogram in FIG. 9, the velocities in FIG. 10 were calculated for a column 2 having a column diameter 7 of 6400 mm. An inlet pipe diameter 6, 17 of in each case 3000 mm, a pressure of 0.025 bar, a gas density of 0.118 kg/m³, a gas viscosity of 7.8·10⁻⁶ Pas, a velocity in the inlet pipes 3, 5 of in each case 11.7 m/s with an F factor of 4 and a velocity in the column 2 of 5.46 m/s with an F factor of 1.87 were prescribed as further boundary conditions.

The intersection of the curves 35, 37, 39 with a cumulated proportion by area 41 of 95% is the velocity which is of such a magnitude that the velocity is greater on only 5% of the cross-sectional area and the intersection of the curves 35, 37, 39 with the cumulated proportion by area 43 of 5% is the velocity which is of such a magnitude that the velocity is lower on only 5% of the cross-sectional area. The difference can then be determined in a simple manner from the graphs. When all curves 35, 37, 39 as depicted here are shown in a graph, the nonuniform distribution can be read off directly. The greater the distance between the intersections of in each case one curve 35, 37, 39 with the straight line 41 or 43, the greater is the nonuniform distribution. In an arrangement of 2 inlet pipes 3, 5, it can thus be seen that the greatest nonuniform distribution occurs at an angle α of the inlet pipes of 180°, so that a smaller angle α should be selected. The difference of the nonuniform distribution for an arrangement of the inlet pipes at 90° or 120° is so much smaller compared to the nonuniform distribution at 180° that the exact angle can, for example, be matched to the circumstances of the piping around the column.

Example 3

Figure 11:
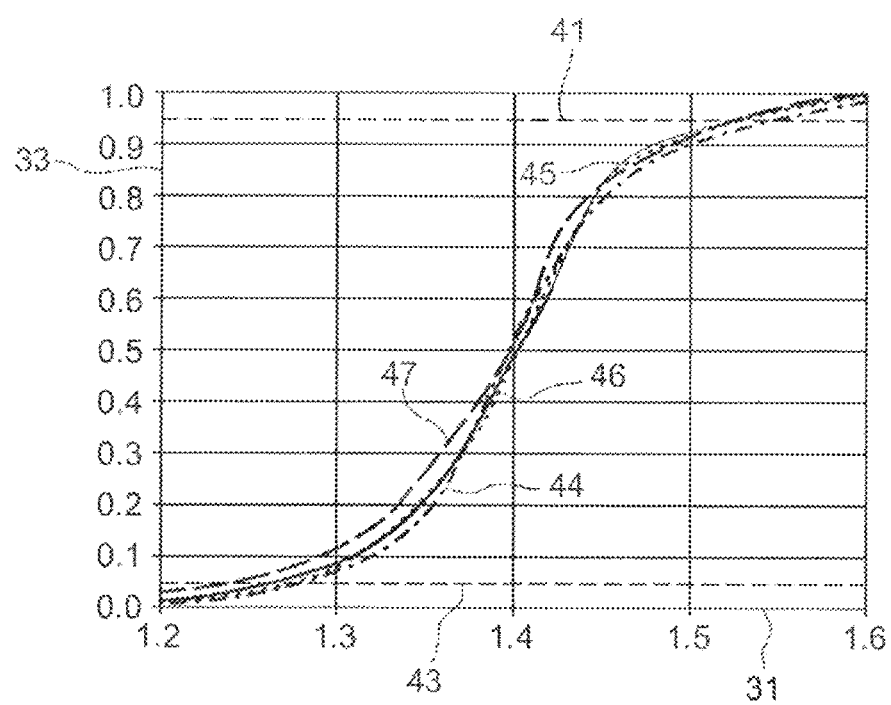

FIG. 11 shows frequency distributions for a column 2 having a column diameter 7 of 2900 mm and an inlet pipe diameter 6, 17 of the inlet pipes 3, 5 of in each case 900 mm. Trays having a pressure drop of 3 mbar at the entry 11 into the separation-active internals 9, i.e. the lowermost tray, were assumed as separation-active internals 9 in the column 2. The calculation was based on an arrangement of two inlet pipes 3, 5 arranged at the same height and at an angle α of 60°, 90°, 120° or 180° from one another in each case.

A pressure in the column 2 of 1.2 bar, a gas density of 1.63 kg/m³, a gas viscosity of 1.2·10-Pa·s, a velocity in the inlet pipes 3, 5 of in each case 7.4 m/s with an F factor of 9.4 and a velocity in the column 2 of 1.82 m/s with an F factor of 1.43 were prescribed as boundary conditions for the calculation of the velocities.

A system of a plurality of eddy structures which are not depicted here and in which flow lines, likewise not depicted here, move upward in the direction of the trays is established in the interior of the column 2. The vertical velocity component at the entry 11 into the lowermost tray is a measure of the incorrect distribution which is established in the column 2.

Cumulated frequency functions were calculated in each case for the different inlet pipe arrangements from the histogram data not shown here in a manner analogous to FIG. 9 and are shown in FIG. 11.

The difference between the velocity which is of such a magnitude that the velocity is greater on only 5% of the cross-sectional area and the velocity which is of such a magnitude that the velocity is lower on only 5% of the cross-sectional area is calculated as measure for the nonuniform distribution. The smaller this difference, the more uniform is the flow distribution.

FIG. 11 shows frequency functions of the relative velocity at the entry 11 into the separation-active internals 9, i.e. into the trays, for the different inlet pipe arrangements. Here, the velocity in m/s is plotted on the abscissa 31 and the cumulated proportion by area from 0 (no proportion at all) to 1 (the total area) is plotted on the ordinate 33.

In a first arrangement, the angle α between the inlet pipes 3, 5 is 60°. The associated fourth curve (broken line) of the frequency function is denoted by the reference symbol 44. A second curve 45 (solid line) shows the frequency function for an arrangement of the inlet pipes 3, 5 at an angle α of 90° from one another, a third curve 46 (dotted line) shows the frequency function for an arrangement of the inlet pipe 3, 5 at an angle α of 120° and a fourth curve 47 (broken line) shows the frequency function for an arrangement of the inlet pipes 3, 5 at an angle α of 180°.

The intersection of the curves 44, 45, 46 and 47 with a cumulated proportion by area 41 of 0.95 is the velocity which is of such a magnitude that the velocity is greater on only 5 out of 100 parts of the cross-sectional area and the intersection of the curves 44, 45, 46 and 47 with the cumulated proportion by area 43 of 0.05 is the velocity which is of such a magnitude that the velocity is lower on only 5 out of 100 parts of the cross-sectional area. The difference can then be determined in a simple manner from the graphs. When all curves 44, 45, 46 and 47 are depicted in a graph, as shown here, the nonuniform distribution can be read off directly. The greater the distance between the intersections of in each case one of the curves 44, 45, 46 and 47 with the straight line 41 or 43, the greater is the nonuniform distribution. In an arrangement of two inlet pipes 3, 5, it can thus be seen that the greatest nonuniform distribution is at the angle α of the inlet pipes of 180° here. The results depicted in FIG. 11 are summarized in table 1.

TABLE 1

| Angle α | Nonuniform distribution at a pressure drop of 3 mbar [%] |
|---|---|
| 60° | 19.3 |
| 90° | 18.6 |
| 120° | 17.9 |
| 180° | 20.0 |

Example 4

Figure 12:
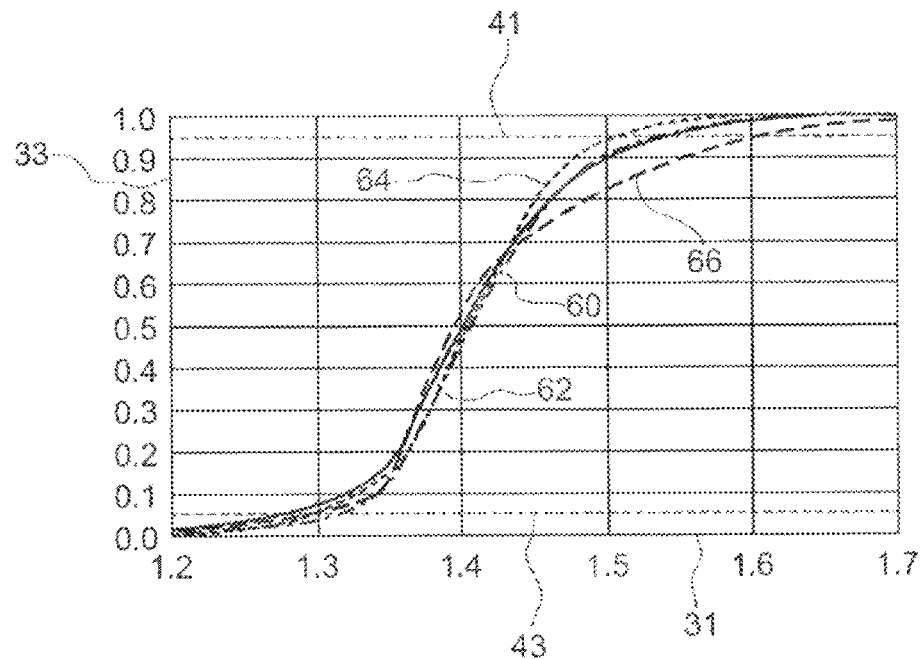

FIG. 12 shows frequency distributions for a column 2 which correspond essentially to the column 2 of example 3. Here, different velocities prevail in the two inlet pipes 3, 5, with the inlet pipe diameters 6, 17 each being 900 mm.

A velocity of 8.9 m/s with an F factor of 11.3 in the first inlet pipe 3 and a velocity of 5.9 m/s with an F factor of 7.5 in the second inlet pipe 5 were used as a basis for the calculation.

FIG. 12 shows, in a manner corresponding to FIG. 11, frequency functions of the relative velocity at the entry 11 into the separation-active internals 9 for different inlet pipe arrangements, with different gas velocities prevailing in the inlet pipes 3, 5 here.

In a first arrangement, the angle α between the inlet pipes 3, 5 is 60°. The associated eighth curve (dash-dot line) of the frequency function is denoted by reference numeral 60. A ninth curve 62 (solid line) shows the frequency function for an arrangement of the inlet pipes 3, 5 at an angle α of 90° from one another, while the tenth curve 64 (dotted line) shows the frequency function for an arrangement of the inlet pipes 3, 5 at an angle α of 120° and an eleventh curve 66 (broken line) shows the frequency function for an arrangement of the inlet pipes 3, 5 at an angle α of 180°.

The greatest nonuniform distribution prevails at the angle α of the inlet pipes of 180°, and the uniformity of the distribution is improved further for the remaining arrangements compared to an embodiment with equal velocities (cf. table 1). The results depicted in FIG. 12 are summarized in table 2.

TABLE 2

| Angle α | Nonuniform distribution at a pressure drop of 3 mbar [%] |
|---|---|
| 60° | 15.6 |
| 90° | 18.6 |
| 120° | 15.1 |
| 180° | 22.0 |

Example 5

Figure 13:
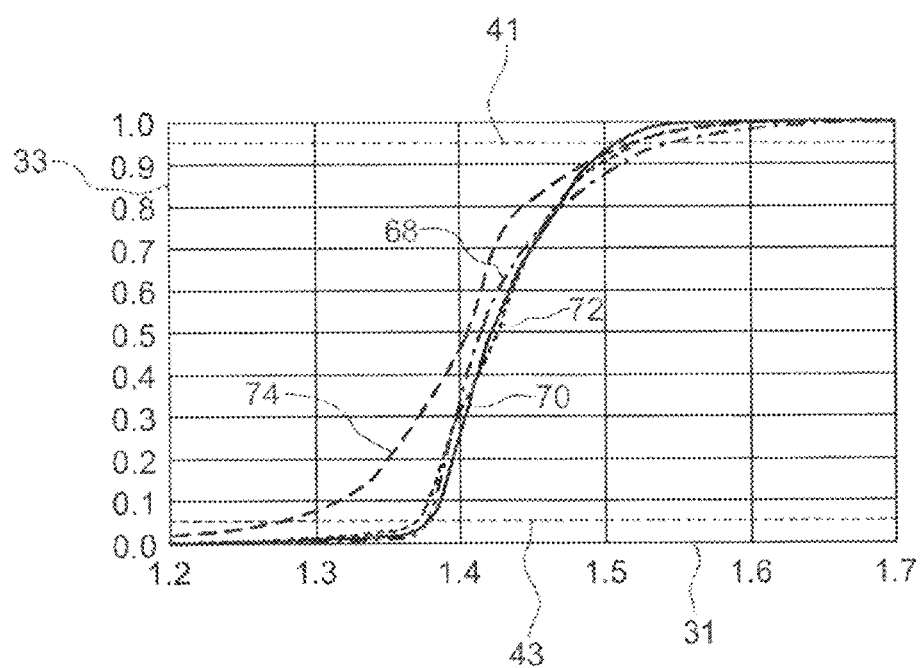

FIG. 13 shows frequency distributions for a column 2 which corresponds essentially to the column 2 of example 3. Here, two inlet pipes 3, 5 with different inlet pipes diameters 6, 17 are present, with the gas velocities in the inlet pipes 3, 5 each being 7.4 m/s with an F factor of 9.4.

An inlet pipe diameter 6 of the first inlet pipe 3 of 794 mm and a further inlet pipe diameter 17 of the second inlet pipe 5 of 995 mm were used as a basis for the calculation.

FIG. 13 shows, in a manner corresponding to FIG. 11, frequency functions of the relative velocity at the entry 11 into the separation-active internals 9 for different inlet pipe arrangements, with the inlet pipes 3, 5 here having different inlet pipe diameters 6, 17.

In a first arrangement, the angle α between the inlet pipes 3, 5 is 60°. The associated twelfth curve (dash-dot line) of the frequency function is denoted by reference numeral 68. A thirteenth curve 70 (solid line) shows the frequency function for an arrangement of the inlet pipes 3, 5 at an angle α of 90° from one another, while a fourteenth curve 72 (dotted line) shows the frequency function for an arrangement of the inlet pipes 3, 5 at an angle α of 120° and a fifteenth curve 74 (broken line) shows the frequency function for an arrangement of the inlet pipes 3, 5 at an angle α of 180°.

The greatest nonuniform distribution prevails at an angle α of the inlet pipes of 180°, with the nonuniform distribution being improved further compared to an embodiment with equal inlet pipe diameters (cf. table 1). The results depicted in FIG. 13 are summarized in table 3.

TABLE 3

| Angle α | Nonuniform distribution at a pressure drop of 3 mbar [%] |
|---|---|
| 60° | 12.1 |
| 90° | 9.3 |
| 120° | 13.7 |
| 180° | 18.2 |

Example 6

Figure 14:
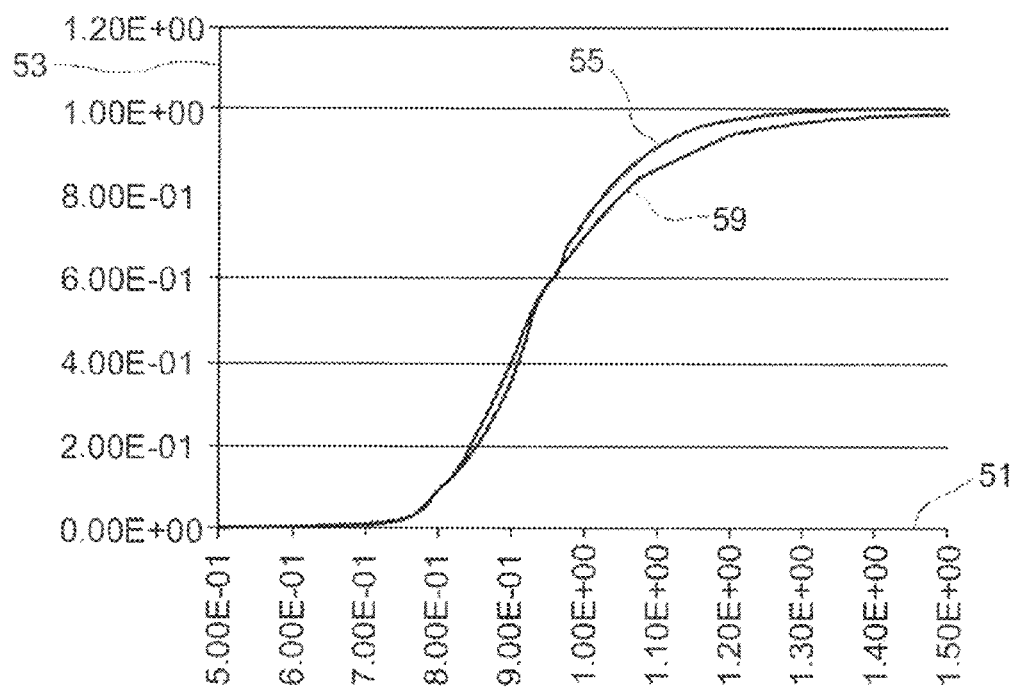

As boundary conditions for FIG. 14, the same conditions as for the depiction in FIG. 9 were selected, except that the velocity in the inlet pipes 3, 5 was increased by a factor of 1.5 and the inlet pipe diameters 6, 17 were correspondingly decreased in order to obtain the same velocity in the column.

For a curve 55 which shows the frequency distribution for two inlet pipes 3, 5, an angle α between the inlet pipes 3, 5 of 120° was prescribed. For the calculation of a curve 59 using only one inlet pipe 3, an inlet pipe 3 enlarged by a factor $2^{0.5}$ in diameter was used. As a result, the F factor and the velocity in the column 2 and thus also the pressure drop in the separation-active internals 9, i.e. the packing, remain constant compared to the introduction of the gaseous phase via two inlet pipes 3, 5.

The normalized velocity is plotted on the abscissa 51 and the proportion by area is plotted on the ordinate 53 here.

The first curve 55 shows the frequency distribution for two inlet pipes 3, 5. The second curve 59 shows the frequency distribution for one inlet pipe 3.

It can clearly be seen from the comparison in FIG. 14 that a better uniform distribution is achieved in the case of a column 2 having two inlet pipes 3, 5.

Example 7

The effects of a nonuniform distribution of a vapor phase exiting from two vaporizers, based on the cross-sectional area of a column, were examined with the aid of a thermodynamic simulation of an overall plant for producing n-butyl acrylate.

The thermodynamic simulation was carried out using the software Aspen Plus®. Model data banks for modeling unit operations and also materials data banks were imported in respect of specific materials properties which are implemented in the software. Mixing properties were calculated by means of the software based on various thermodynamic models of materials data of the pure substances.

Example 7a

Figure 15:
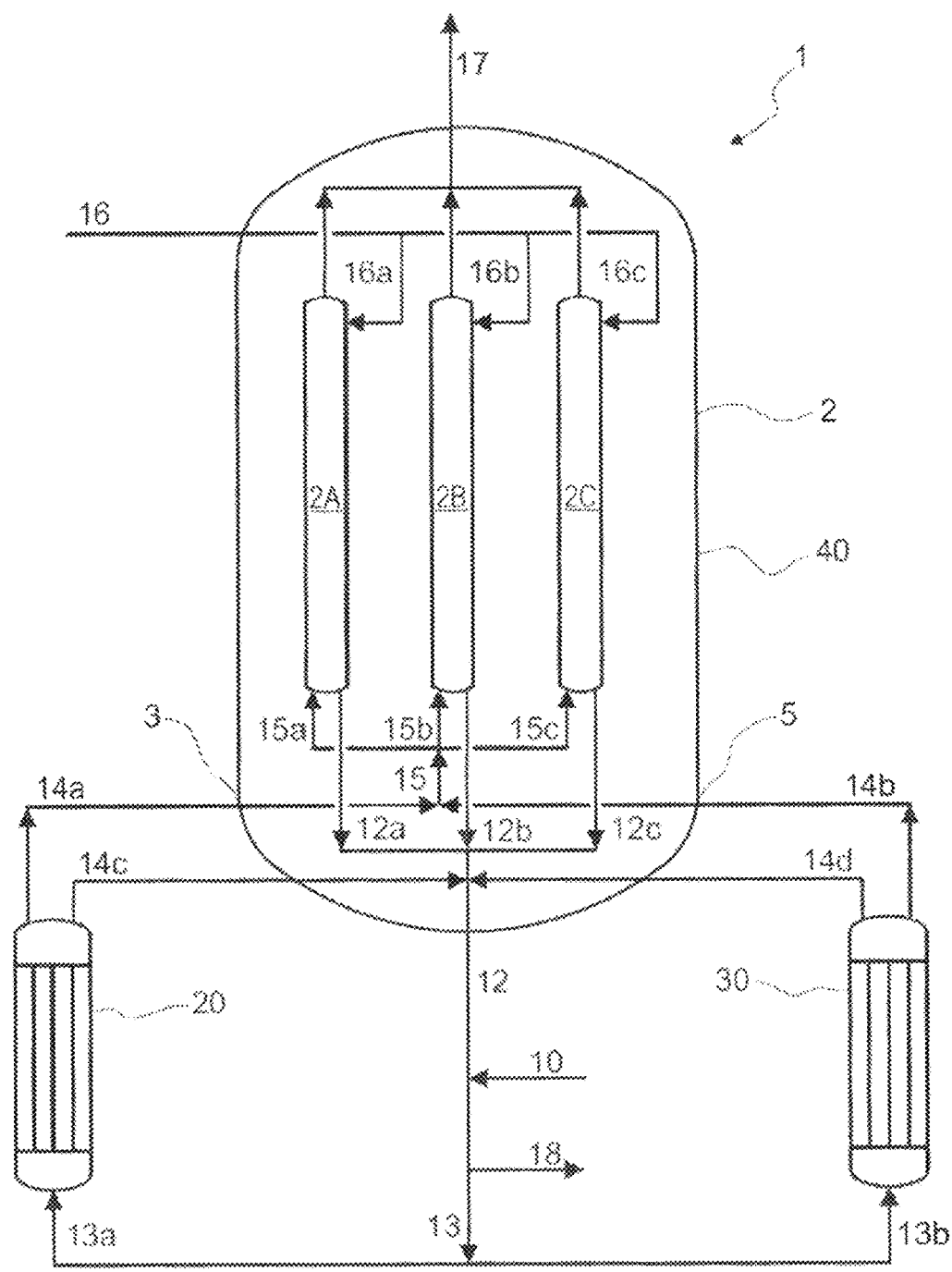

To determine the energy consumption in the case of a uniformly distributed gaseous phase, three vapor streams 15a, 15b, 15c having an identical size, as are depicted in FIG. 15, were used as a basis.

A column 2 as rectification column 40 was represented with three identical subcolumns 2A, 2B, 2C in the simulation and the three subcolumns 2A, 2B, 2C were each simulated with 13 theoretical plates.

At the top of the subcolumns 2A, 2B, 2C, a runback 16 in the form of a liquid phase was divided into three equal-sized liquid streams 16a, 16b, 16c and distributed over the three subcolumns 2A, 2B, 2C.

At the bottom of the column, bottom offtake streams 12a, 12b, 12c and liquid streams 14c, 14d exiting from vaporizers 20, 30 were combined to form a total stream 12, i.e. a liquid phase from the column 2, and mixed with a feed stream 10. A small substream 18 of the total stream 12 was discharged from the plant and the main stream 13 of the total stream 12 was divided into two identically sized streams 13a, 13b and fed to the two vaporizers 20, 30.

Vapor streams 14a, 14b which exit from the vaporizers 20, 30 and were fed, for example, through inlet pipes 3, 5 to the column 2 were combined to form a vapor feed stream 15 and then divided into three identically sized streams 15a, 15b, 15c, each in the form of a gaseous phase, and introduced into the three subcolumns 2A, 2B, 2C.

The division of the vapor feed stream 15 was effected equally:
Vapor stream (15a) 33.33% by weight,
Vapor stream (15b) 33.33% by weight,
Vapor stream (15c) 33.33% by weight, in each case based on the vapor feed stream 15.

The thermodynamic simulation of the total plant indicated the following quantities of heat required in the vaporizers 20, 30:

Vaporizer 20: 8922 kW, Vaporizer 30: 8922 kW.

Example 7b

To determine the energy consumption in the case of an unequally divided gaseous phase, three unequal vapor streams 15a, 15b, 15c as per FIG. 15 were used as a basis. The procedure was otherwise as in example 7a.

A nonuniform distribution of the vapor streams 14a, 14b exiting from the vaporizers 20, 30 over the cross-sectional area of the column 2, which is caused by an unfavorable arrangement of the inlet pipes 3, 5 at the circumference of the column, was simulated by the different-sized vapor streams 15a, 15b, 15c which were fed to the subcolumns 2A, 2B, 2C.

The division of the vapor feed stream 15 was effected unequally:
Vapor stream (15a) 31.33% by weight,
Vapor stream (15b) 33.33% by weight,
Vapor stream (15c) 35.33% by weight, in each case based on the vapor feed stream 15.

All other conditions remained unchanged compared to example 7a.

The thermodynamic simulation of the total plant indicated the following quantities of heat required in the vaporizers 20, 30:
Vaporizer (20): 9237 kW,
Vaporizer (30): 9237 kW.

Compared to example 7a, about 3.5% more energy was required in the two vaporizers in the case of the nonuniform introduction of vapor.

Local ratios of liquid phase and gaseous phase in the rectification column 40 were changed by the nonuniform distribution of the gaseous phase fed in. In order to fulfil the same separation task in the rectification column 40 as in example 7a, more energy is required than in the case of a uniform distribution of the gaseous phase.

A comparison of examples 7a and 7b taking into account examples 1 to 6 shows that the energy consumption for the same separation performance is reduced by a uniform distribution of the gaseous phase over the cross-sectional area of a column 2, in particular a rectification column 40, which is achieved by a configuration according to the invention of the inlet pipes 3, 5.

LIST OF REFERENCE SYMBOLS

1 Apparatus for carrying out mass transfer processes
2 Column
2A, 2B, 2C Subcolumns
3 First inlet pipe
4 Radial direction
5 Second inlet pipe
6 Inlet pipe diameter
7 Column diameter
8 Height
9 Separation-active internals
10 Feed stream
11 Entry
12 Total stream, liquid phase
12a, 12b, 12c Bottom offtake streams
13 Main stream
13a, 13b Streams of the main stream
14a, 14b Exiting vapor streams
14c, 14d Exiting liquid streams
15 Vapor feed stream
15a, 15b, 15c Vapor streams of the vapor feed stream
16 Runback
16a, 16b, 16c Liquid streams
17 Further inlet pipe diameter
18 Substream
19 Circumference
20 First vaporizer
21 Abscissa, velocity
23 Ordinate, cross-sectional area
25 Third inlet pipe
27 Fourth inlet pipe
28 Section height
29 Column section
30 Second vaporizer
31 Abscissa, relative velocity
33 Ordinate, cumulated proportion by area
35 First curve of the frequency function
37 Second curve of the frequency function
39 Third curve of the frequency function
40 Rectification column
41 Cumulated proportion by area of 95%
43 Cumulated proportion by area of 5%
44 Fourth curve of the frequency function
45 Fifth curve of the frequency function
46 Sixth curve of the frequency function
47 Seventh curve of the frequency function
51 Abscissa, normalized velocity
53 Ordinate, proportion by area
55 First curve of the frequency distribution
59 Second curve of the frequency distribution
60 Eighth curve of the frequency function
62 Ninth curve of the frequency function
64 Tenth curve of the frequency function
66 Eleventh curve of the frequency function
68 Twelfth curve of the frequency function
70 Thirteenth curve of the frequency function
72 Fourteenth curve of the frequency function
74 Fifteenth curve of the frequency function
$\alpha$ Angle
$\beta$ Further angle

The invention claimed is:

1. An apparatus (1) for carrying out mass transfer processes, comprising a column (2) having at least two inlet pipes (3, 5) for introducing a gaseous phase,
   wherein separation-active internals (9) are accommodated in the column (2) and a column section (29) extends from the at least two inlet pipes (3, 5) to the separation-active internals (9),
   wherein in the column section a coverage of a cross-sectional area of the column (2) is less than 25%, based on the total cross-sectional area, and
   wherein the at least two inlet pipes (3, 5) have a height offset which corresponds to not more than three times the largest inlet pipe diameter (6) and the at least two inlet pipes (3, 5) are at an angle ($\alpha$) of from 60° to 150° to one another and have asymmetry with respect to one another,
   wherein the asymmetry is given by the at least two inlet pipes (3, 5) each having different inlet pipe diameters (6, 17).

2. The apparatus (1) according to claim 1, wherein the asymmetry is given by the at least two inlet pipes (3, 5) being distributed asymmetrically around the circumference (19) of the column (2).

3. The apparatus (1) according to claim 1, wherein the angle (α) differs by at least 10° from a further angle (β) between two of the at least two inlet pipes (3, 5).

4. The apparatus (1) according to claim 1, wherein the at least two inlet pipes (3, 5) are arranged at the same height (8) on the column (2).

5. The apparatus (1) according to claim 1, wherein the at least two inlet pipes (3, 5) are arranged at the bottom of the column (2) or as side inlet on the column (2).

6. The apparatus according to claim 1, wherein the apparatus (1) comprises precisely two inlet pipes (3, 5) for introducing a gaseous phase, where the two inlet pipes (3, 5) have a height offset which corresponds to not more than three times the largest inlet pipe diameter (6).

7. The apparatus (1) according to claim 1, wherein the at least two inlet pipes (3, 5) open radially into the column (2).

8. The apparatus (1) according to claim 1, wherein the separation-active internals (9) comprise a structured packing and/or packing elements.

9. The apparatus (1) according to claim 1, wherein the separation-active internals (9) comprise trays without guided flow.

10. The apparatus (1) according to claim 1, wherein the separation-active internals (9) comprise crossflow trays.

11. The apparatus (1) according to claim 1, wherein vaporizers (20, 30) are attached via the at least two inlet pipes (3, 5) to the column (2).

12. A method comprising carrying out a mass transfer process in the apparatus (1) according to claim 1, for producing isocyanates, styrene or an alkyl acrylate.

13. The method according to claim 12, wherein the asymmetry is given by the flow velocities through the at least two inlet pipes (3, 5) being different.

14. The method according to claim 12, wherein the apparatus (1) for carrying out mass transfer processes is used as rectification column (40) in a process for the continuous production of an alkyl acrylate ($H_2C$=CH—C(=O)OR, where R=n-butyl or isobutyl), wherein aqueous 3-hydroxypropionic acid is reacted under dehydrating and esterifying conditions in the presence of the appropriate butanol (R—OH) in a reactor comprising the rectification column (40) and butyl acrylate formed, unreacted butanol and also water used and water formed are distilled off as ternary azeotrope at the top and, after separation into a respectively liquid aqueous phase and liquid organic phase, the aqueous phase and the organic phase are each at least partly discharged and the organic phase comprising the butyl acrylate and the butanol is fractionally distilled.

15. The method according to claim 12, wherein a liquid phase (12) is taken off from the rectification column (40), at least partially vaporized and at least partly recirculated via the at least two inlet pipes (3, 5) to the rectification column (40).

16. The method according to claim 15, wherein the liquid phase (12) is at least partially vaporized in at least two vaporizers (20, 30).

17. The method according to claim 12, wherein the pressure at the top of the rectification column (40) is in the range from 0.2 bar to 5.0 bar absolute.

18. The method according to claim 14, wherein the fractional distillation of the organic phase comprising the butyl acrylate and the butanol is carried out by distilling off the butanol in an additional rectification column (40) and distilling off the butyl acrylate from the resulting bottoms in a further additional rectification column (40).

\* \* \* \* \*